US00PP15162P2

(12) United States Plant Patent
Mansur Vergara et al.

(10) Patent No.: US PP15,162 P2
(45) Date of Patent: Sep. 21, 2004

(54) GLORY OF THE SUN PLANT NAMED 'GABRIELA'

(50) Latin Name: *Leucocoryne*
Varietal Denomination: Gabriela

(75) Inventors: Leví Mansur Vergara, Los Andes (CL); Gabriela Verdugo Ramírez, Quillota (CL)

(73) Assignee: Pontificia Universidad Catolica De Valparaiso, Valparaiso (CL)

( * ) Notice: Subject to any disclaimer, the term of this patent is extended or adjusted under 35 U.S.C. 154(b) by 0 days.

(21) Appl. No.: 10/455,333

(22) Filed: Jun. 6, 2003

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—Foley & Lardner LLP

(57) ABSTRACT

A new and distinct cultivar of the Glory of the Sun plant named 'Gabriela' characterized by having: very hard scape; green, white and violet-blue obovate tepals; pleasant aroma; yellow-green staminodes; and tepals with shiny and waxy bases.

3 Drawing Sheets

Latin name of the genus and species of the plant claimed: Leucocoryne (species unknown).
Variety denomination: Gabriela.

BACKGROUND OF THE INVENTION

The present invention relates to a new and distinct cultivar of the Glory of the Sun plant, known in Chile as Huilli and botanically known as Leucocoryne (species unknown). The new cultivar is referred to herein by the cultivar name 'Gabriela.' Leucocoryne are bulbous herbs that are native to Chile.

The new cultivar was selected from a population grown in a cultivated area (greenhouse) in Chile in 1998 by the inventors, Leví Mansur Vergara and Gabriela Verdugo Ramírez. The population from which the instant cultivar was selected originated from uncontrolled crosses among unknown parent plants. Asexual propagation has demonstrated that the combination of characteristics as herein disclosed for the new cultivar are firmly fixed and retained through successive generations of asexual reproduction. The new cultivar was asexually reproduced in a cultivated area (greenhouse) in Chile from 1999. The method used to asexually reproduce was natural bulbification. The new cultivar reproduces true-to-type.

BRIEF SUMMARY OF THE INVENTION

The following traits have been repeatedly observed and are determined to be basic characteristics of 'Gabriela' which in combination distinguish this Glory of the Sun as a new and distinct cultivar:

1. Very hard scape;
2. Tepal shape: Obovate;
3. Tepal color: Base green, RHS 143 B; middle portion white, RHS 155 C; apex violet-blue, RHS 91 C;
4. Aroma: Pleasant;
5. Staminode color: Yellow-green 154 D; and
6. Tepals with a shiny and waxy base.

'Gabriela' has not been observed under all possible environmental conditions. The phenotype of the new cultivar, with the exception of flower design, as shown in the second drawing sheet, may vary with variations in environment such as temperature, light intensity, and day length without any change in the genotype of the plant. However, the phenotype is reproduced true-to-type under the environmental conditions in which they were observed. The following observations, measurements and values describe the new cultivar as grown in Quillota, Chile (32° 53' lat. S; 71° 16' long. W) under conditions that favor normal Leucocoryne growth.

BRIEF DESCRIPTION OF THE DRAWING

There are three accompanying drawings that illustrate the overall appearance of the new Glory of the Sun cultivar 'Gabriela'. These show the umbel, the flower, and the foliage of 'Gabriela'. The images portray colors as true as is reasonably possible with colored reproductions of this type.

The first photographic drawing shows the umbel of 'Gabriela', depicting a cluster of inflorescences and buds.

The second photographic drawing shows a close-up of the flower of 'Gabriela' and the third photographic drawing shows the foliage of an adult plant of 'Gabriela'.

DETAILED BOTANICAL DESCRIPTION

The following observations, measurements and values describe the new cultivar as grown in Quillota, Chile (32° 53' lat. S; 71° 16' long. W) under conditions that favor normal Leucocoryne growth. The Glory of the Sun cultivar 'Gabriela' has been grown in unheated greenhouses from March to November, under a temperature regime as described in Table 1 below:

TABLE 1

Temperature data in Quillota, Chile (32° 53' lat. S; 71° 16' long. W).

| Month | Temperature (Celsius) Maximum | Minimum | Minimum Absolute | Average |
|---|---|---|---|---|
| March | 25.6 | 9.8 | 5.30 | 17.70 |
| April | 27.7 | 8.1 | 3.60 | 15.40 |
| May | 19.9 | 7.4 | 2.70 | 13.65 |
| June | 16.9 | 5.8 | 0.90 | 11.35 |
| July | 16.8 | 5.5 | 0.40 | 11.15 |
| August | 18.2 | 5.8 | 0.10 | 12.00 |
| September | 19.7 | 6.9 | 2.40 | 13.30 |
| October | 21.9 | 8.2 | 3.30 | 15.05 |
| November | 24.7 | 9.1 | 5.20 | 16.90 |

Color references are made to The Royal Horticultural Society Colour Chart (R.H.S.), except where general colors of ordinary significance are used. Color values were taken under daylight conditions, approximately in September in Quillota. The plant characteristics described below are based on observations of adult plants capable of flowering with bulb weighing over 1.0 gram, as grown in a container (20 cm diameter, 22 cm depth).

Parentage:
- *Male parent.*—Leucocoryne (species unknown, unpatented).
- *Female parent.*—Leucocoryne (species unknown, unpatented).

Plant:
- *General appearance and form.*—Form: Geophytic herb. Height (typical): 55 cm. Height (range): 45–65 cm. Growth habit: Erect.

Foliage:
- *Overall shape of leaf.*—Linear.
- *Maximum length* (*typical*).—36 cm.
- *Maximum width* (*range*).—30–41 cm.
- *Width* (*typical*).—5.0 mm.
- *Width* (*range*).—4.0–6.0 mm.
- *Apex.*—Rounded.
- *Margin.*—Entire.
- *Color.*—Green-Yellow (Munsell 5GY 5/4; 5GY 6/4; and 5GY 6/6) (both upper and lower surfaces).

Scape:
- *Length* (*typical*).—50 cm.
- *Length* (*range*).—40–60 cm.
- *Diameter* (*typical*).—3.8 mm.
- *Diameter* (*range*).—2.8–4.4 mm.
- *Texture.*—3 (on a scale of 1=soft, 2=hard, 3=very hard).
- *Color.*—Green-Yellow (Munsell 5GY 4/6; 5GY 5/6; 5GY 5/8; and 5GY 5/10).

Spathes:
- *Spathes per umbel.*—2.
- *Shape.*—Linear-lanceolate.
- *Length* (*typical*).—3.8 cm.
- *Length* (*range*).—3.5–4.0 cm.

Umbels:
- *Depth* (*typical*).—7 cm.
- *Depth* (*range*).—4–9 cm.
- *Diameter* (*typical*).—11 cm.
- *Diameter* (*range*).—8–13 cm.
- *Number of flower per umbel* (*typical*).—6.
- *Number of flower per umbel* (*range*).—3–8.
- *Bulbils.*—None.

Pedicel:
- *Length* (*typical*).—3.5 cm.
- *Length* (*range*).—1.5–6.0 cm.

Flower:
- *Depth* (*typical*).—1.6 cm.
- *Depth* (*range*).—1.5–1.7 cm.
- *Diameter* (*typical*).—5.9 cm.
- *Diameter* (*range*).—5–6.3 cm.
- *Tepals per flower.*—6.
- *Aroma.*—Pleasant.
- *Lastingness of the bloom.*—10 weeks.

Tepal:
- *Shape.*—Obovate.
- *Apex.*—Obtuse.
- *Base.*—Acute.
- *Margin.*—Entire.
- *Length* (*typical*).—2.7 cm.
- *Length* (*range*).—2.3–3.0 cm.
- *Color.*—Base, green, RHS 143 B; middle portion, white, RHS 155 C; apex, violet-blue RHS 91 C (upper and lower surfaces).

Bulb:
- *Shape.*—Globular, somewhat flattened basally.
- *Diameter.*—Typical equatorial diameter of adult bulb: 2.0–3.0 cm. Max equatorial observed: 3.2 cm.
- *Weight.*—Typical fresh weight of adult bulb: 3.0–9.0 grams. Max fresh weight of adult bulb: 9.7 grams.
- *Skin color.*—Greyed-orange, RHS N163 A; 167 A; and 167 B.
- *Dropper per bulb.*—0–2.

Dropper: Stolon-like structure that grows from the bulb and produces a bulb at the tip.
- *Dropper shape.*—Ovate (elongated-oval).
- *Diameter equatorial.*—1.2–1.5 cm.
- *Weight.*—1.2–1.6 gr.
- *Dropper skin color.*—Greyed-orange, RHS N163 A; 167 A; and 167 B.

Reproductive Organs:
- *Anthers.*—Quantity: 3. Size: 2.5–3.0 mm. Color: Yellow (Munsell 5Y 8/12).
- *Staminodes.*—Quantity: 3. Size: 6.0–7.0 mm. Color: Yellow-green RHS 154 D.
- *Pistils.*—1 per flower.
- *Stigma and styles.*—Style short and cylindrical; stigma somewhat capitate.
- *Ovaries.*—Quantity: 1. Size: 4.5–5.5 mm. Color: Green-Yellow (Munsell Color Chart 7.5GY 8/2; 7.5GY 8/4; and 7.5GY 8/6).
- *Pollen.*—Viable.
- *Seed.*—Viable. Amount (typical): 35 per fruit. Amount (range): 22–44 per fruit. Size: 1.5 mm.

Disease resistance/susceptibility: No information to date.

Pest resistance/susceptibility: Susceptible to *Pseudococcus affinis.*

We claim:

1. A new and distinct cultivar of the Glory of the Sun plant named 'Gabriela', substantially as illustrated and described herein.

* * * * *

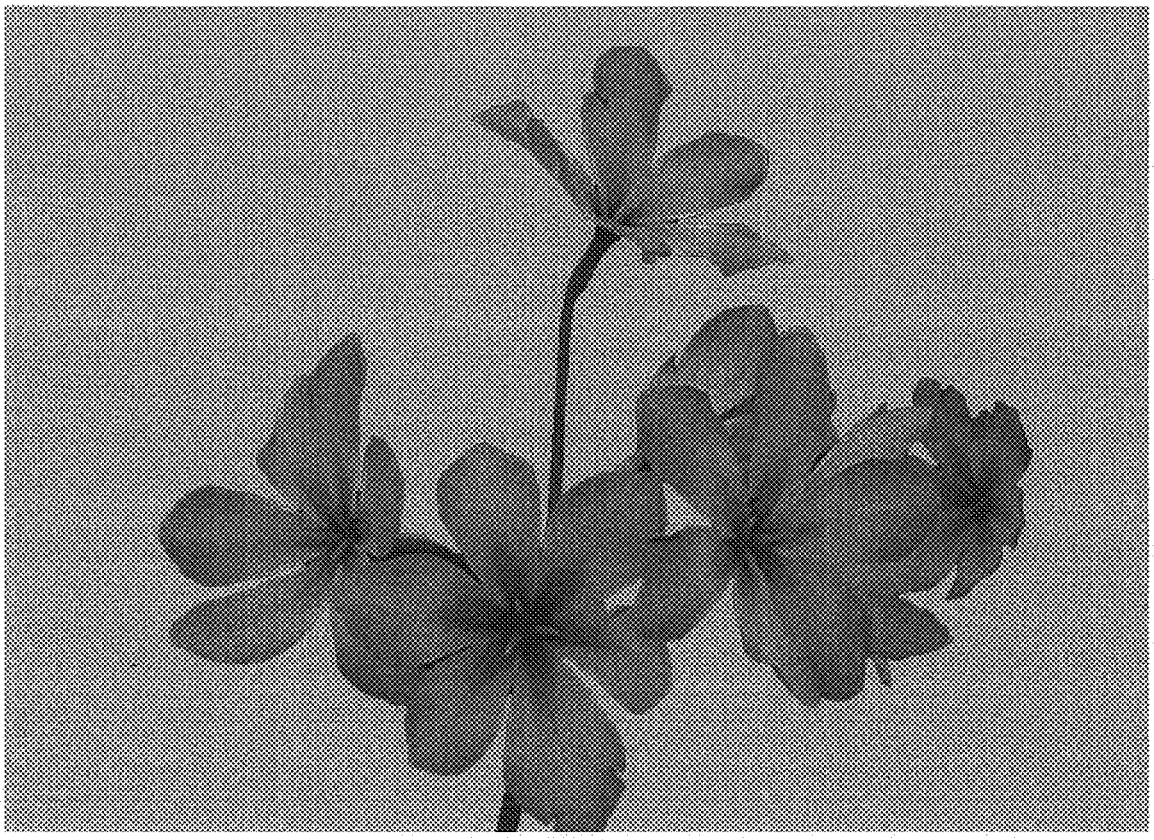

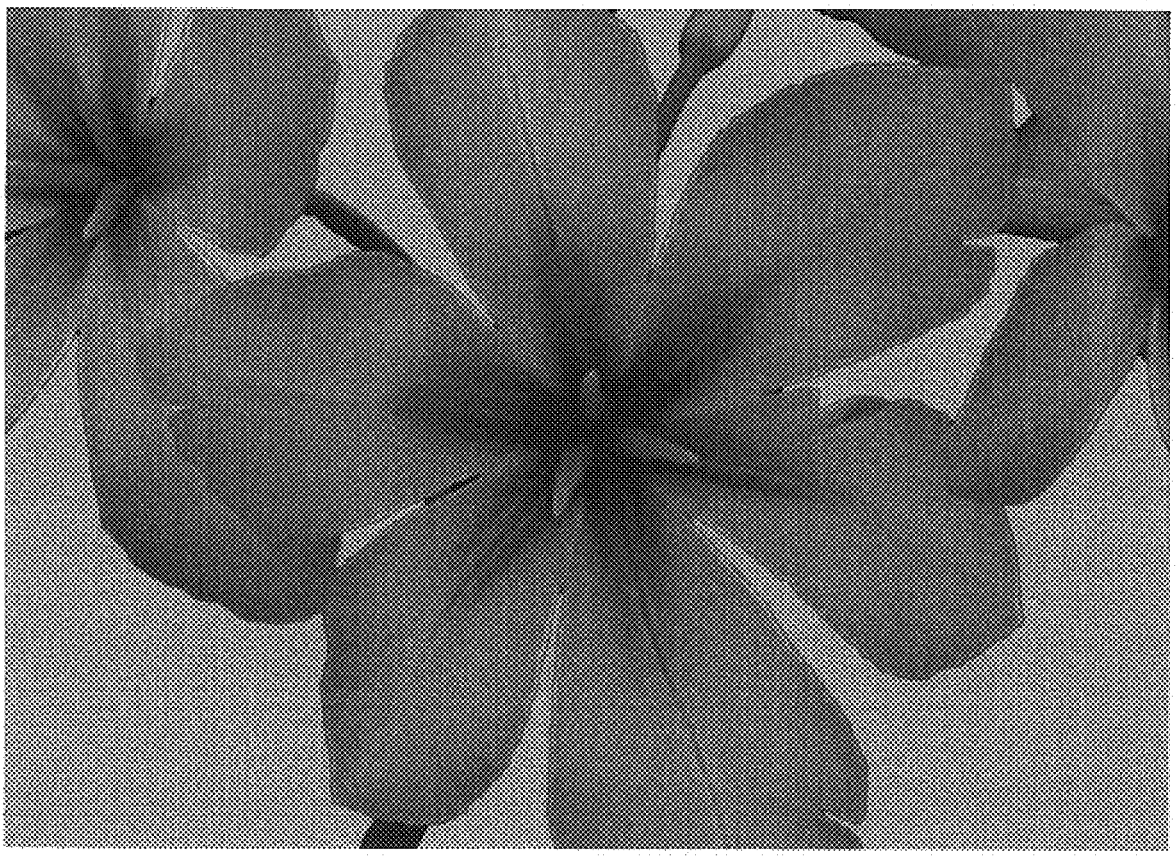

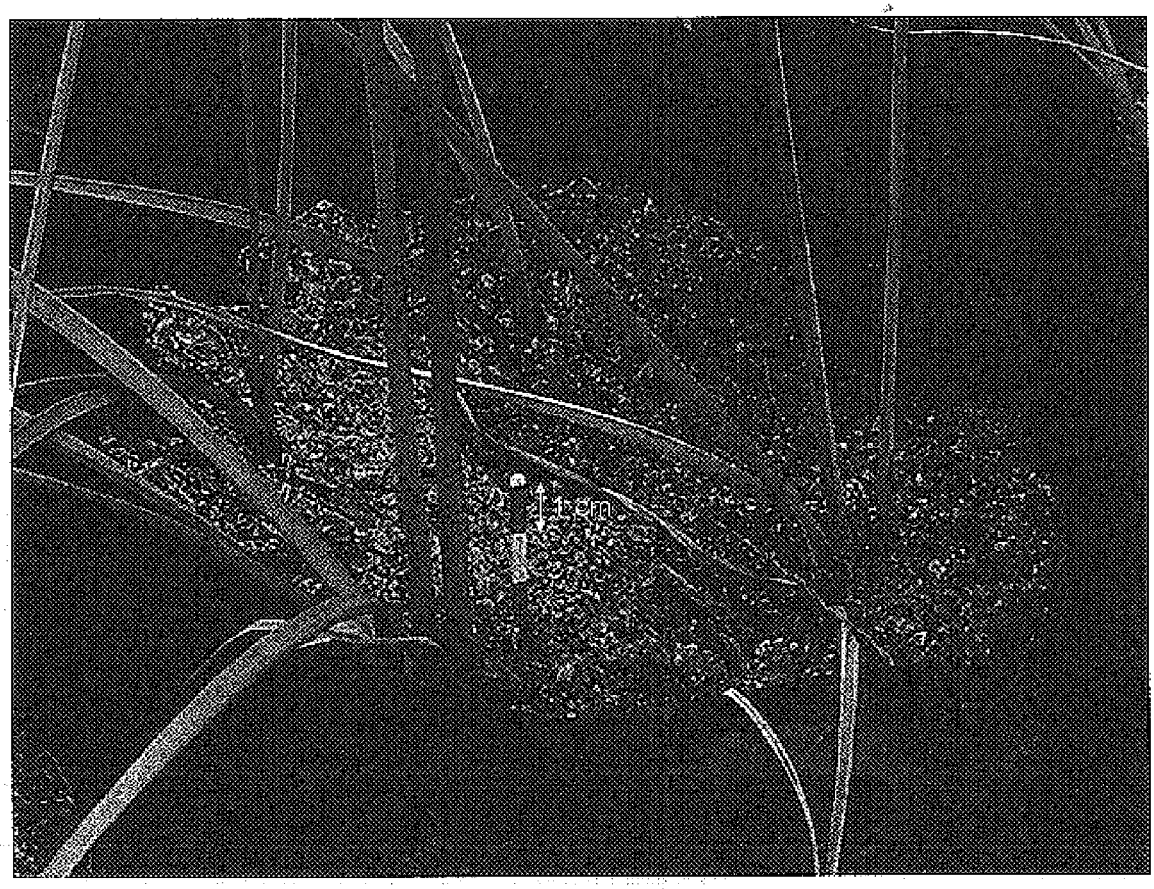
1cm